United States Patent [19]

Young

[11] Patent Number: 5,422,242
[45] Date of Patent: Jun. 6, 1995

US005422242A

[54] MYCOBACTERIUM PRIMERS AND PROBES

[75] Inventor: Karen K. Y. Young, San Ramon, Calif.

[73] Assignee: Hoffmann-La Roche Inc., Nutley, N.J.

[21] Appl. No.: 915,922

[22] Filed: Jul. 17, 1992

Related U.S. Application Data

[63] Continuation-in-part of Ser. No. 746,704, Aug. 15, 1991, abandoned.

[51] Int. Cl.$^6$ .......................... C12Q 1/68; C12Q 1/04; C07H 17/00
[52] U.S. Cl. .......................................... 435/6; 435/34; 536/24.3; 536/24.32; 536/24.33
[58] Field of Search ...................... 435/6, 34; 536/24.3, 536/24.32, 24.33

[56] References Cited

U.S. PATENT DOCUMENTS

| | | | |
|---|---|---|---|
| 4,683,195 | 7/1987 | Mullis et al. | 435/6 |
| 4,851,330 | 7/1989 | Kohne | 435/6 |
| 4,965,188 | 10/1990 | Mullis et al. | 435/6 |

FOREIGN PATENT DOCUMENTS

| | | |
|---|---|---|
| 0398677 | 5/1989 | European Pat. Off. |
| 8402721 | 7/1984 | WIPO |
| 8403957 | 7/1988 | WIPO |

OTHER PUBLICATIONS

Saiki et al., 1988, N. Eng. J. Med. 319:537–541.
Saiki et al., 1989, Proc. Natl. Acad. Sci. 86:6230–6234.
AmpliType DQalpha DNA Typing Kit Package Insert.
Brisson-Noel et al., 1989, Lancet 334:1069–1071.
Hance et al., 1989, Molecular Microbiology 3(7):843–849.
Woods and Cole, 1989, FEMS Microbiology Letters 65:305–310.
Pao et al., 1990, J. Clin. Microbiol. 28(9):1877–1880.
Hackel et al., 1990, Molecular and Cellular Probes 4:205–210.
Hartskeerl et al., 1989, J. Gen. Microbiol. 135:2357–2364.
Eisenach et al., 1990, J. Infectious Disease 161:977–981.
Thierry et al., 1990, J. Clin. Microbiol. 28(12):2668–2673.
Plikaytis et al., 1991, Molecular and Cellular Probes 5:215–219.
DeWitt et al., 1990, J. Clin. Microbiol. 28(11):2437–2441.
Vary et al., 1990, J. Clin. Microbial. 28(5):933–937.
Sjobring et al., 1990, J. Clin Microbiol. 28(10):2200–2204.
Shankar et al., 1990, Lancet 335:423.
Patel et al., 1990, J. Clin. Microbiol. 28(3):513–518.
Fries et al., 1990, Molecular and Cellular Probes 4:87–105.
Suzuki et al., 1988, J. Bacteriol. 170(6):2886–2889.
Bottger, 1989, FEMS Microbiology Letters 65:171–176.
Neefs et al., 1990, Nuc. Acids Res. Supplement 18:2237–2317.
Liesack et al., 1990, Nuc. Acids Res. 18(19):5558.
Edwards et al., 1989, Nuc. Acids Res. 17:7843–7853.
Stahl and Urabance, 1990, J. Bacteriol. 172(1):116–124.
Rogall et al., 1990, J. Gen. Micro. 136:1915–1920.
Boddinghaus et al., 1990, J. Clin. Microbiol. 28(8):1751–1759.

*Primary Examiner*—Robert A. Wax
*Assistant Examiner*—Keith D. Hendricks
*Attorney, Agent, or Firm*—George M. Gould; Dennis P. Tramaloni; Douglas A. Petry

[57] ABSTRACT

Primers and probes can be used to detect nucleic acid from Mycobacterium in a sample and determine the species from which the nucleic acid originates. The primers amplify regions of the 16S ribosomal RNA gene and hybridize to regions conserved among species. Genus specific probes hybridize to sequences within the amplified region conserved among mycobacterial species, whereas the species specific probes hybridize to a variable region, so that the species identity can be uniquely determined. Consensus probes for detecting mycobacteria nucleic acids are provided which probes are not identical to any of the sequences of mycobacterial species.

18 Claims, 1 Drawing Sheet

FIG. 1

GENUS SPECIFIC PROBES

KY:21
KY:63
KY:26
KY:25
KY:139
KY:106

Ye Ph Fo Ch Fl Sm Ma Sc Go Ka In Av Tb

MYCOBACTERIUM PRIMERS AND PROBES

CROSS-REFERENCE

This application is a continuation-in-part of U.S. Ser. No. 07/746,704, filed Aug. 15, 1991, now abandoned.

BACKGROUND OF THE INVENTION

1. Field of the Invention

The present invention relates to methods and reagents for detecting the presence of mycobacterial nucleic acid and identifying the mycobacterial species from which a mycobacterial nucleic acid in a sample originates.

2. Description of Related Art

Mycobacteria are slow growing, acid-fast, aerobic bacilli. At least nineteen Mycobacterium species have so far been associated with disease in humans, most notably *M. tuberculosis*, *M. bovis*, and *M. leprae*. Some species, such as *M. avium*, *M. intracellulare*, and *M. kansasii*, though not normally pathogenic to healthy individuals, may cause disease in immunocompromised individuals, such as those infected with the ADS virus. In addition, several species rarely cause disease in humans but may occur in clinical specimens as saprophytes. Methods for the detection and identification of Mycobacterium species include bacterial culture, antibody detection, and, more recently, detection of rRNA by hybridization with a radioactively labelled nucleic acid probe. Each of these methods has considerable problems.

Detection by culturing the bacilli is slow, requiring up to two months, and typically requires additional biochemical testing for species identification. Antibody detection lacks specificity because of cross-reactivity between mycobacteria species and also lacks sensitivity. Furthermore, differentiation between current and past infections is difficult. Detection using radioactively labelled DNA fragments as probes that hybridize to the small subunit ribosomal RNA (16S rRNA) lacks sensitivity and still requires at least a several-day culturing period (see PCT/WO 84/02721).

The invention of the polymerase chain reaction (PCR), a method for amplifying specific sequences of nucleic acids, makes possible the rapid detection of nucleic acids present in a cell in what was previously an undetectably low quantity. Using PCR amplification, one can detect even a single copy of the target nucleic acid. Direct detection by hybridization with a sequence-specific oligonucleotide probe of a nucleic acid sequence amplified to a detectable level makes possible diagnostic tests that are specific enough to detect single nucleotide changes in sequence. However, not all primer pairs and probes are useful. The choice of primers and, hence, the region to be amplified, along with the choice of probes largely determines the specificity and sensitivity obtainable.

Amplification by the PCR hits been used in the sequencing of mycobacterial nucleic acid, detection of mycobacterial nucleic acids in a sample, and identification of mycobacteria species. Various regions of the bacterial genome have been used to detect and identify mycobacterial nucleic acids in samples. Most of these diagnostic tests were designed to detect only one or a small number of species, and limited specificity checks, if any, were performed against non-mycobacterial DNA.

Detection of a region of the gene that encodes the 65 kilodalton antigen was described in Chia et al., 1990, *J. Clin. Microbiol.* 28(9):1877–1880; Brisson-Noel et al., 1989, *Lancet* 334:1069–1071; Hackel et al., 1990, *Molecular and Cellular Probes* 4:205–210; Woods and Cole, 1989, *FEMS Microbiology Letters* 65:305–310; and Hance et al., 1989, *Molecular Microbiology* 3(7):843–849. No more than three sets of mycobacteria species were distinguished in any one test based on the 65 kilodalton antigen gene.

Amplification of the repetitive DNA element, IS6110, was reported in Thierry et al., 1990, *J. Clin. Microbiol.* 28(12):2668–2673, and Eisenach et al., 1990, *J. Infectious Disease* 161:977–981. Amplification of IS6110 basically serves only to test for the presence of particular species of mycobacteria, although *M. tuberculosis* and *M. bovis* can be distinguished by copy number (Plikaytis et al., 1991, *Molecular and Cellular Probes* 5:215–219).

The 36 kilodalton antigen of *M. leprae* was used in a diagnostic test in Hartskeerl et al., 1989, *J. Gen. Microbiol.* 135:2357–2364. Though the test was meant to be specific for *M. leprae*, weak to moderate hybridization to DNA from other mycobacteria was observed.

The gene sequence coding for protein antigen b was used in Sjobring et al., 1990, *J. Clin. Microbiol.* 28(10):2200–2204, to produce a test for *M. tuberculosis/bovis* based on the presence or absence of an amplified product.

A test solely for the presence of *M. tuberculosis* based on the gene sequence encoding the MPB 64 protein was described in Shankar et al., 1990, *Lancet* 335:423.

Probes constructed from cloned DNA fragments were described in Patel et al., 1990, *J. Clin. Microbiol.* 28(3):513–518, and Fries et al., 1990, *Molecular and Cellular Probes* 4:87–105. Probe specificity was obtained through a selection process rather than by sequence analysis during the probe design.

One of the regions of the mycobacterial genome that has been analyzed and targeted for use in a diagnostic test is the small subunit ribosomal RNA (16S rRNA). In Bottger, 1989, *FEMS Microbiology Letters* 65:171–176, the 16S rRNA genes from a variety of organisms were amplified using "universal" primers designed to amplify nucleic acid from a wide range of organisms and then directly sequenced. The phylogenetic relationship of mycobacterial species was studied by comparing 16S rRNA germ sequences in Rogall et al. 1990, *J. Gen. Micro.* 136:1915–1920. In Boddinghaus et al., 1990, *J. Clin. Microbiol.* 28(8): 1751–1759, evidence was presented regarding determinations that can be made using sequence specific oligonucleotides for amplification and hybridization to regions of the 16S rRNA sequence. A highly variable region of the 16S rRNA sequence was studied with respect to three mycobacteria species. Genus specific primers were used to amplify a region containing the variable region used for species specific probe hybridization.

The small subunit rRNA from a large number of organisms, both closely and distantly related to mycobacteria, has been studied and sequenced. A compilation of small subunit rRNA sequences from a large number of organisms is provided by Neefs et al., 1990, *Nuc. Acids Res. Supplement* 18:2237–2317.

There is still a need for a rapid and sensitive test to identify the presence of mycobacterial DNA and the species from which the DNA originates.

SUMMARY OF THE INVENTION

The present invention provides a rapid and sensitive PCR based assay for the detection and species identification of mycobacteria. Primers and probes specific for 16S ribosomal RNA gene sequences are provided. Mycobacteria detection is accomplished by amplification with genus specific primers followed by screening with genus specific probes in a dot blot hybridization assay. If mycobacteria are detected, species identification is determined from amplified DNA, normally from the same amplification reaction, using the species specific probes in a reverse dot blot assay.

The amplification of sequences encoding the 16S ribosomal RNA (rRNA) has several advantages. The present invention can be used to detect and distinguish between more than 30 mycobacterial species and numerous other organisms that might be present in a clinical sample. The probes and primers of the present invention provide the maximum specificity possible, thereby minimizing the probability of a false positive caused by the presence of a related organism with a similar sequence. The 16S rRNA gene contains highly conserved regions. The genus specific primers and probes of the present invention hybridize to such conserved regions and are able to hybridize to sequences from almost all species in the genus; the primers amplify nucleic acid from 14 of the 15 mycobacterial species tested, and of these 14 amplified mycobacterial DNA sequences, the genus specific probes hybridize to 12. The 16S rRNA also contains highly variable regions within the amplified region. The species specific probes of the present invention hybridize in a variable region where each species of interest has a unique sequence.

An additional advantage of choosing primers and probes from the 16S rRNA is that the rRNA is present in a growing cell in large copy numbers ($10^3$ to $10^4$). The number of gene sequences in the form of RNA in a given clinical sample would be, therefore, up to $10^4$ times greater than the number of the corresponding DNA sequences. If additional detection sensitivity is desired, the RNA itself can be used as the amplification target.

In another aspect of the invention, a second amplification reaction is carried out as a confirmatory test. The second amplification reaction relies on the presence of target sequences not directly related to the first target, i.e., the 16S ribosomal RNA nucleic acids. Suitable target sequences are preferably conserved among Mycobacterium species and are not related to non-Mycobacterium species. A suitable target gene may be, for example, the gene encoding the 65 kDa protein gene. Pao et al., 1989, *FEMS Micro. Letters* 65:305-310; Hartskeerl et al., 1989, *J. Gen. Micro.* 135:2357-2364; and Hackel et al., 1990; *Mol. Cel. Probes* 4:205-210. While useful for confirming the results of a first amplification reaction, the amplification of a second target sequence is particularly meaningful for resolving discordant results that may arise from comparative studies, notably the comparison of PCR and culture methods.

An additional aspect of the present invention relates to novel compositions for use as positive controls for detecting Mycobacterium. The invention provides a novel composition for confirming the results of an assay using genus specific probes as well as species specific Mycobacterium probes.

One aspect of the invention relates to probes capable of detecting the presence of Mycobacterium nucleic acid (genus specific probes) and determining the identity of the species from which the nucleic acid originates (species specific probes).

Another aspect of the invention relates to consensus probes. In the preferred embodiment the invention provides consensus oligonucleotides for the amplification and detection of disparate species of Mycobacterium isolates. The consensus oligonucleotide probes do not hybridize to non-Mycobacterium species that are closely related to mycobacteria.

Consensus probes are suitable for a broad range of target-specific detection using a single oligonucleotide probe. A consensus probe, as used herein, is an oligonucleotide probe which is not identical in sequence to any of the mycobacteria nucleic acid sequences to be detected. The consensus probes are hybrid oligonucleotide compositions comprising non-native nucleic acid sequences. Consensus probes as described in the present invention can be used to exclude as well as to include selected species in a detection assay. In one embodiment, the invention provides oligonucleotide probes comprising novel sequences. While these probes broadly detect mycobacterial species, they do not detect closely related non-mycobacterial species, for example, Corynebacter.

Another aspect of the invention relates to primers for amplifying a specific region of mycobacteria nucleic acid. This region contains both a region conserved among Mycobacterium species and a variable region with sufficient heterogeneity among species to enable the origin of the target nucleic acid to be determined using sequence specific oligonucleotide probes.

Another aspect of the invention relates to detection and species identification methods. Amplification of the target nucleic acid by PCR, using the primers of the invention, allows one to detect the presence of mycobacterial nucleic acid by mixing the amplified nucleic acid with the genus specific probes and detecting if hybridization occurs, whereas species identification is carried out by determining the pattern of hybridization to the species specific probes.

A fourth aspect of the invention relates to kits. These kits take a variety of forms and comprise one or more probes and, in one embodiment, comprise a panel of probes sufficient to determine the identity of an infecting Mycobacterium at the species level and instructions for using the kit ingredients. The kits can also comprise one or more amplification reagents, e.g., genus specific primers, polymerase, buffers, and nucleoside triphosphates.

In a further embodiment, the kit may also comprise positive and negative controls. A preferred positive control is described herein.

To aid in understanding the invention, several terms are defined below.

The term "oligonucleotide" refers to a molecule comprised of two or usually more deoxyribonucleotides or ribonucleotides, such as primers, probes, nucleic acid fragments to be detected, and nucleic acid controls. The exact size of an oligonucleotide depends on many factors and the ultimate function or use of the oligonucleotide. Oligonucleotides can be prepared by any suitable method, including, for example, cloning and restriction of appropriate sequences and direct chemical synthesis by a method such as the phosphotriester method of Narang et al., 1979, *Meth. Enzymol.* 68:90-99; the phosphodiester method of Brown et al., 1979, *Meth. Enzymol.* 68:109-151; the diethylphosphoramidite method of Beaucage et al., 1981, *Tetrahedron Lett.* 22:1859-1862; and the solid support method of U.S. Pat. No. 4,458,066.

The term "primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different deoxyribonucleoside triphosphates and an agent for polymerization (i.e., DNA polymerase or reverse transcriptase) in an appropriate buffer and at a suitable temperature. A primer is preferably a single-stranded oligodeoxyribonucleotide. The appropriate length of a primer depends on the intended use of the primer but typically ranges from 15 to 25 nucleotides. Short primer molecules generally require cooler temperatures to form sufficiently stable hybrid complexes with the template. A primer need not reflect the exact sequence of the template but must be sufficiently complementary to hybridize with a template and serve to initiate DNA synthesis.

In the disclosed embodiments of the invention, specific sequence primers and probes are provided. It will be apparent to those of skill in the art that, provided with those embodiments, specific sequence primers and probes can be modified by, for example, the addition of nucleotides to either the 5' or 3' ends, which nucleotides are complementary to the target sequence or are uncomplementary to the target sequence. So long as primer compositions serve as a point of initiation for extension on the target sequences, and the primers and probes comprise at least 14 consecutive nucleotides contained within those exemplified embodiments, such compositions are within the scope of the invention.

The term "primer" may refer to more than one primer, particularly in the case where there is some ambiguity in the information regarding one or both ends of the target region to be amplified. If a "conserved" region shows significant levels of polymorphism in a population, mixtures of primers can be prepared that will amplify such sequences, or the primers can be designed to amplify even mismatched sequences. A primer can be labeled, if desired, by incorporating a label detectable by spectroscopic, photochemical, biochemical, immunochemical, or chemical means. For example, useful labels include $^{32}P$, fluorescent dyes, electron-dense reagents, enzymes (as commonly used in ELISAs), biotin, or haptens and proteins for which antisera or monoclonal antibodies are available. A label can also be used to "capture" the primer, so as to facilitate the immobilization of either the primer or a primer extension product, such as amplified DNA, on a solid support.

The terms "sequence specific oligonucleotide" and "SSO" refer to oligonucleotides that have a sequence, called a "hybridizing region", complementary to the sequence to be detected, which, under "sequence specific, stringent hybridization conditions", will hybridize only to that exactly complementary target sequence. Relaxing the stringency of the hybridization conditions will allow sequence mismatches to be tolerated; the degree of mismatch tolerated can be controlled by suitable adjustment of the hybridization conditions. The terms "probe" and "SSO probe" are used interchangeably with SSO.

The term "target region" refers to a region of a nucleic acid to be analyzed.

The term "thermostable polymerase enzyme" refers to an enzyme that is relatively stable to heat and catalyzes the polymerization of nucleoside triphosphates to form primer extension products that are complementary to one of the nucleic acid strands of the target sequence. The enzyme initiates synthesis at the 3'-end of the primer and proceeds in the direction toward the 5'-end of the template until synthesis terminates. A purified thermostable polymerase enzyme is described more fully in U.S. Pat. No. 4,889,818, incorporated herein by reference, and is commercially available from Perkin Elmer (Norwalk, Conn.).

The term "reverse transcriptase" refers to an enzyme that catalyzes the polymerization of nucleoside triphosphates to form primer extension products that are complementary to a ribonucleic acid template. The enzyme initiates synthesis at the 3'-end of the primer and proceeds in the direction toward the 5' end of the template until synthesis terminates. Examples of suitable polymerizing agents that convert the RNA target sequence into a complementary, copy DNA (cDNA) sequence are avian myeloblastosis virus reverse transcriptase and *Thermus thermophilus* DNA polymerase, a thermostable DNA polymerase with reverse transcriptase activity marketed by Perkin Elmer.

BRIEF DESCRIPTION OF THE DRAWING

FIG. 1 shows the results of hybridization tests using both the genus specific and species specific probes of the invention. The specificity of the probes was tested with DNA from thirteen different species of Mycobacterium.

DETAILED DESCRIPTION OF THE INVENTION

The present invention provides a rapid and sensitive PCR based assay for the detection and species identification of Mycobacterium. Primers and probes specific for mycobacterial 16S ribosomal RNA gene sequences are provided. Mycobacterial detection is accomplished by amplification with genus specific primers followed by screening with genus specific probes in a dot blot hybridization assay. If mycobacteria are detected, species identification is determined from DNA from the same amplification reaction using the species-specific probes in a reverse dot-blot assay. Both the forward and reverse dot blot assays can be carried out very conveniently in a microtiter plate; see U.S. patent application Ser. No. 414,542, filed Sep. 29, 1989, incorporated herein by reference.

The genus specific primers and probes hybridize to conserved regions of the 16S rRNA gene, and the species specific probes hybridize to variable regions of the 16S rRNA gene. Because synthesis starts at the 3' end of the primer, mismatches at the 3' end are more critical. Thymidine is more tolerant than the other bases of a mismatch; so primers were designed to avoid a thymidine base at the 3' end. The base content of an oligonucleotide affects the denaturation temperature. The stringency and specificity of primer or probe binding increases with increasing temperature. However, because all probes are hybridized simultaneously in the reverse dot-blot format, optimal probe hybridization conditions are similar for all the probes.

The primer pairs of the invention function efficiently in the amplification of a sequence of the 16S rRNA gene from all the Mycobacterium species of interest but do not amplify the corresponding DNA from most other sources. Furthermore, the amplification conditions and efficiency for these primers are fairly uniform across species so that nearly all Mycobacterium species are detectable using a single test. Table 1 shows the hybridizing sequences of the primers of the present invention.

TABLE I

| Primer | Sequence Listing | Hybridizing Sequence |
|---|---|---|
| KY18 | SEQ ID NO: 1 | 5' CACATGCAAGTCGAACGGAAAGG 3' |
| KY75 | SEQ ID NO: 2 | 5' GCCCGTATCGCCCGCACGCTCACA 3' |

Using the *E. coli* numbering system, the upstream primer, KY18 (SEQ ID NO: 1), spans bases 52–74, and the downstream primer, KY75 (SEQ ID NO: 2), spans bases 624–647 of the 16S rRNA gene. Together, these primers specify the synthesis of a product approximately 583 base-pairs in length; the exact size is species dependent.

The initial screening for the presence of mycobacterial DNA is accomplished with two genus specific probes that are used simultaneously as a mixture.

TABLE 2

| Probe | Sequence Listing | Hybridizing Sequence |
|---|---|---|
| KY101 | SEQ ID NO: 3 | 5' TCGCGTTGTTCGTGAAATCTCACgGCTTAA 3' |
| KY102 | SEQ ID NO: 4 | 5' TCGCGTTGTTCGTGAAAaCTCACAGCTTAA 3' |
| KY165 | SEQ ID NO. 13 | 5' TCGCGTTGTTCGTGAAATCTCACAGCTTAA 3' |
| KY166 | SEQ ID NO. 14 | 5' TCGCGTTGTTCGTGgAATCTCACAGCTTAA 3' |
| M. xenopi | SEQ ID NO. 15 | 5' TCGCGTTGTTCGTGgAATgcCACAGCTTAA 3' |

The reason for the mixed probes is that most mycobacteria species can be divided into two groups with respect to the sequences in the region of KY101 (SEQ ID NO. 3) and KY102 (SEQ ID NO. 4). These two probes detect DNA from 12 out of 14 species of the genus Mycobacterium tested.

In an alternative embodiment, KY165 (SEQ ID NO. 13) replaces probes KY101 (SEQ ID NO. 3) and KY102 (SEQ ID NO. 4). The sequence of probes KY101 (SEQ ID NO. 3), KY102 (SEQ ID NO. 4), KY165 (SEQ ID NO. 13), and KY166 (SEQ ID NO. 14) are given in Table 2. KY165 (SEQ ID NO. 13) is a consensus probe encompassing the sequences of both KY101 (SEQ ID NO. 3) and KY102 (SEQ ID NO. 4). KY101 (SEQ ID NO. 3) and KY102 (SEQ ID NO. 4) differ from each other by two bases. KY165 (SEQ ID NO. 13) is not identical to either KY101 (SEQ ID NO. 3) or KY102 (SEQ ID NO. 4), but differs from each by a single base. This consensus was arrived at by "favoring" KY101 (SEQ ID NO. 3) in one of the mismatched positions and KY102 (SEQ ID NO. 4) in the other mismatched positions. KY165 (SEQ ID NO. 13) is able to hybridize sufficiently to all KY101 (SEQ ID NO. 3) and KY102-specific (SEQ ID NO. 4) mycobacterial species. KY165 (SEQ ID NO. 13) does not hybridize to *M. xenopi* (SEQ ID NO. 15) under conditions of high stringency due to the presence of additional mismatches.

KY166 (SEQ ID NO. 14) is a broader consensus probe for detecting mycobacterial species including *M. xenopi* (SEQ ID NO. 15). The sequence of KY166 (SEQ ID NO. 14), like the sequence of KY165 (SEQ ID NO. 13), does not correspond to any non-mycobacterial species. The probe is designed to be equally dissimilar to KY101 (SEQ ID NO. 3), KY102 (SEQ ID NO. 4), and the corresponding sequence in *M. xenopi* (SEQ ID NO. 15) (GenBank accession No. X52929, available through Intelligenetics) KY166 (SEQ ID NO. 14) differs from KY101 (SEQ ID NO. 3), KY102 (SEQ ID NO. 4), and *M. xenopi* (SEQ ID NO. 15) by two bases each. KY166 (SEQ ID NO. 14) efficiently hybridizes to all KY101 (SEQ ID NO. 3) and KY102 (SEQ ID NO. 4) specific species and *M. xenopi* (SEQ ID NO. 15). In addition, KY166 (SEQ ID NO. 14) does not hybridize to *Corynebacter pseudodiphtheriticum* or *C. diphtheriae*, two non-mycobacterial species that are closely related to Mycobacterium. The corresponding sequence of *M. xenopi* (SEQ ID NO. 15) is included in Table 2. In the Table, the mismatches relative to KY166 (SEQ ID NO. 14) are underlined. Mismatches relative to KY165 (SEQ ID NO. 13) are in lower case.

If mycobacterial nucleic acid is present in the sample, the species from which the nucleic acid originates can be determined by hybridization to a panel of species specific probes. The probes used in the species identification step are shown in Table 3.

TABLE 3

| Probe | Sequence Listing | Specificity |
|---|---|---|
| KY21 | SEQ ID NO: 5 | *M. tuberculosilis/bovis*/tb |
| | 5' ACGGGATGCATGTCTTGTGGTGGAAAGCGCTTTAGC 3' | |
| KY25 | SEQ ID NO: 6 | *M. kansasii/gastri/scrofulaceum* |
| | 5' ACTTGGCGCATGCCTTGTGGTGGAAAGCTT 3' | |
| KY26 | SEQ ID NO: 7 | *M. intacellulare* |
| | 5' TTTAGGCGCATGTCTTTAGGTGGAAAGCTT 3' | |
| KY63 | SEQ ID NO: 8 | *M. avium/maringum/microti* |
| | 5' TCAAGACGCATGTTCTTCTGGTGGAAAGCTTTTGC 3' | |
| KY151 | SEQ ID NO: 9 | *M. marinum/M. microti* |
| | 5' TCCCGAAGTGCAGGCCAGATTGCCCACGTG 3' | |
| KY106 | SEQ ID NO: 10 | *M. scrofulaceum* |
| | 5' GAAGGCTCACTTTGTGGGTTGACGGTAGGT 3' | |
| KY126 | SEQ ID NO: 11 | *M. kansasii/gastri* |
| | 5' GCAATCTGCCTGCACACCGGGATAAGCCTG 3' | |
| KY139 | SEQ ID NO: 12 | *M. gordonae* |
| | 5' GGGTCTAATACCGAATAGGACCACAGGACACATG 3' | |
| KY157 | SEQ ID NO: 16 | *M. xenopi* |
| | 5' ATAGGACCATTCTGCGCATGTGGTGTGGTG 3' | |
| KY167 | SEQ ID NO: 17 | *M. avium/marinun/microti* |
| | 5' ACCTCAAGACGCATGTCTTCTGGT 3' | |
| KY168 | SEQ ID NO: 18 | *M. gordonae* |

TABLE 3-continued

| Probe | Sequence Listing | Specificity |
|---|---|---|
| | 5' CCGAATAGGACCACAGGACACATG 3' | |
| KY169 | SEQ ID NO: 19 | M. intracellulare |
| | 5' ACCTTTAGGCGCATGTCTTTAGGT 3' | |
| KY170 | SEQ ID NO: 20 | M. kansasii/gastri/scrofulaceum |
| | 5' AACACTTGGCGCATGCCTTGTGGT 3' | |
| KY171 | SEQ ID NO: 21 | M. scrofulaceum |
| | 5' GAAGGCTCACTTTGTGGGTTGACG 3' | |
| KY172 | SEQ ID NO: 22 | M. bovis/tb |
| | 5' TGTGGTGGAAAGCGCTTTAGCGGT 3' | |
| KY173 | SEQ ID NO: 23 | M. xenopi |
| | 5' AGGACCATTCTGCGCATGTGGTGT 3' | |

The species of greatest clinical interest are M. tuberculosis, M. kansasii, M. xenopi, M. intracellulare, and M. avium, M. gordonae is not ordinarily associated with disease but frequently occurs in human samples. Consequently, detection of mycobacterial nucleic acid by the genus specific probes is expected frequently to be due to the clinically unimportant M. gordonae. Example 6 contains additional information regarding the specificity of the species specific probes.

An important aspect of the present invention is the amplification of a region of the 16S rRNA gene. Those practicing the present invention should note that, although the polymerase chain reaction is the preferred amplification method, amplification of target sequences in a sample may be accomplished by any known method, such as ligase chain reaction (LCR), transcription amplification, and self-sustained sequence replication, each of which provides sufficient amplification so that the target sequence can be detected by nucleic acid hybridization to an SSO probe. Alternatively, methods that amplify the probe to detectable levels can be used, such as Qβ-replicase amplification. The term "probe" encompasses the sequence specific oligonucleotides used in the above procedures; for instance, the two or more oligonucleotides used in LCR are "probes" for purposes of the present invention, even though LCR only requires ligation of the probes to indicate the presence of the sequence.

Although the PCR process is well known in the art (see U.S. Pat. Nos. 4,683,195; 4,683,202; and 4,965,188, each of which is incorporated herein by reference) and although commercial vendors, such as Perkin Elmer, sell PCR reagents and publish PCR protocols, some general PCR information is provided below for purposes of clarity and full understanding of the invention to those unfamiliar with the PCR process.

To amplify a target nucleic acid sequence in a sample by PCR, the sequence must be accessible to the components of the amplification system. In general, this accessibility is ensured by isolating the nucleic acids from the sample. A variety of techniques for extracting nucleic acids from biological samples are known in the art. For example, see those described in Higuchi et al., 1989, in *PCR Technology* (Erlich ed., Stockton Press, New York). Alternatively, if the sample is fairly readily disruptable, the nucleic acid need not be purified prior to amplification by the PCR technique, i.e., if the sample is comprised of cells, particularly peripheral blood lymphocytes or aminiocytes, lysis and dispersion of the intracellular components can be accomplished merely by suspending the cells in hypotonic buffer.

Each cycle of the PCR involves the separation of the nucleic acid duplex formed by primer extension. In a preferred embodiment of the PCR process, strand separation is achieved by heating the reaction to a sufficiently high temperature for an effective time to cause the denaturation of the duplex, but not to cause an irreversible denaturation of the polymerase (see U.S. Pat. No. 4,965,188). Typical heat denaturation involves temperatures ranging from about 80° C. to 105° C. for times ranging from seconds to minutes. Strand separation, however, can be accomplished by any suitable denaturing method including physical, chemical, or enzymatic means. Strand separation can be induced by a helicase, for example, or an enzyme capable of exhibiting helicase activity. For example, the enzyme RecA has helicase activity in the presence of ATP. The reaction conditions suitable for strand separation by helicases are known in the art (see Kuhn Hoffman-Berling, 1978, *CSH-Quantitative Biology* 43:63–67; and Radding, 1982, *Ann. Rev. Genetics* 16:405–436).

No matter how strand separation is achieved, however, once the strands are separated, the next step in PCR involves hybridizing the separated strands with primers that flank the target sequence. The primers are then extended to form complementary copies of file target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

Template-dependent extension of primers in PCR is catalyzed by a polymerizing agent in the presence of adequate amounts of four deoxyribonucleoside triphosphates (dATP, dGTP, dCTP, and dTTP; dUTP is used in place of or in addition to dTTP if the UNG sterilization system described below is incorporated) in a reaction medium comprised of the appropriate salts, metal cations, and pH buffering system. Suitable polymerizing agents are enzymes known to catalyze template-dependent DNA synthesis. Examples of polymerases suitable for use with a DNA template include *E. coli* DNA polymerase I or the Klenow fragment of that enzyme, T4 DNA polymerase, and Taq polymerase, a heat stable DNA polymerase isolated from *Thermus aquaticus* and commercially available from Perkin Elmer. The latter enzyme is widely used in the amplification and sequencing of nucleic acids. The reaction conditions for using Taq polymerases are known in the art and are described in Gelfand, 1989, in *PCR Technology*, supra. Polymerizing agents suitable for synthesizing a complementary, copy DNA (cDNA) sequence from the RNA template are reverse transcriptase (RT), such as avian myeloblastosis virus RT, or *Thermus thermophilus* DNA polymerase, a thermostable DNA polymerase with reverse transcriptase activity marketed by Perkin Elmer. Typically, the RNA template is heat degraded during the first denaturation step after the initial reverse transcription step leaving only DNA template for subsequent amplification.

If 16S rRNA is to be amplified, an initial reverse transcription (RT) step is carried out to create a DNA copy (cDNA) of the RNA. PCT patent publication No. WO 91/09944, published Jul. 11, 1991, incorporated herein by reference, describes high temperature reverse transcription by a thermostable polymerase that also functions in PCR amplification. High temperature RT provides greater primer specificity and improved efficiency. Copending U.S. patent application Ser. No. 746,121, Attorney Docket No. 2532.3, inventors Gelfand and Myers, filed Aug. 15, 1991, incorporated herein by reference, describes a "homogeneous RT-PCR" in which the same primers and polymerase suffice for both the reverse transcription and the PCR amplification steps, and the reaction conditions are optimized so that both reactions occur without a change of reagents. *Thermus thermophilus* DNA polymerase, a thermostable DNA polymerase that can function as a reverse transcriptase, is used for all primer extension steps, regardless of template. Both processes can be done without having to open the tube to change or add reagents; only the temperature profile is adjusted between the first cycle (RNA template) and the rest of the amplification cycles (DNA template).

The PCR method can be performed in a step wise fashion, where after each step new reagents are added, or in a fashion where all of the reagents are added simultaneously, or in a partial step wise fashion, where fresh or different reagents are added after a given number of steps. For example, if strand separation is induced by heat, and the polymerase is heat sensitive, then the polymerase has to be added after every round of strand separation. However, if, for example, a helicase is used for denaturation, or if a thermostable polymerase is used for extension, then all of the reagents may be added initially, or, alternatively, if molar ratios of reagents are of consequence to the reaction, the reagents may be replenished periodically as they are depleted by the synthetic reaction.

Those skilled in the art will know that the PCR process is most usually carried out as an automated process with a thermostable enzyme. In this process, the temperature of the reaction mixture is cycled through a denaturing region, a primer annealing region, and a reaction region. A machine specifically adapted for use with a thermostable enzyme is commercially available from Perkin Elmer.

Those skilled in the art will also be aware of the problem of contamination of a PCR by the amplified nucleic acid from previous reactions. Methods to reduce this problem are provided in PCT patent application Ser. No. US 91/05210, filed Jul. 23, 1991, and U.S. patent application Ser. No. 609,157, filed Nov. 2, 1990, each of which is incorporated herein by reference. The methods allow the enzymatic degradation of any amplified DNA from previous reactions. The PCR amplification is carried out in the presence of dUTP instead of dTTP. The resulting double stranded uracil containing product is subject to degradation by uracil N-glycosylase (UNG), whereas normal thymine-containing DNA is not degraded by UNG. Adding UNG to the amplification reaction mixture before the amplification is started degrades all uracil containing DNA that might serve as target. Because the only source of uracil containing DNA is the amplified product of a previous reaction, this method effectively sterilizes the reaction mixture, eliminating the problem of contamination from previous reactions (carryover). UNG is rendered temporarily inactive by heat, so the denaturation steps in the amplification procedure also serve to inactivate the UNG. New amplification products, therefore, though incorporating uracil, are formed in an UNG-free environment and are not degraded.

Sequence specific probe hybridization is an important step in successful performance of the present methods. The sequence specific oligonucleotide probes of the present invention hybridize specifically with a particular segment of the mycobacterial genome and have destabilizing mismatches with the sequences from other organisms in the case of genus specific probes, and other mycobacteria species, in the case of species-specific probes. Stringent hybridization conditions may be chosen so that the probes hybridize specifically only to exactly complementary sequences. Detection of the amplified product utilizes this sequence specific hybridization to insure that only the correct amplified target is detected, decreasing the chance of a false positive caused by the presence of homologous sequences from related organisms.

The assay methods for detecting hybrids formed between SSO probes and nucleic acid sequences can require that the probes contain additional features in addition to the hybridizing region. In the dot blot format, for example, the probes are typically labelled. If the probe is first immobilized, as in the "reverse" dot blot format described below, the probe can also contain long stretches of poly-dT that can be fixed to a nylon support by irradiation, a technique described in more detail in PCT Patent Publication No. 89/11548, incorporated herein by reference.

The probes of the invention can be synthesized and labeled using the techniques described above for synthesizing oligonucleotides. For example, the probe may be labeled at the 5'-end with $^{32}P$ by incubating the probe with $^{32}P$-ATP and kinase. A suitable non-radioactive label for SSO probes is horseradish peroxidase (HRP). Methods for preparing and detecting probes containing this label are described in U.S. Pat. Nos. 4,914,210 and 4,962,029, each of which is incorporated herein by reference. For additional information on the use of such labeled probes, see U.S. Pat. No. 4,789,630; Saiki et al., 1988, *N. Eng. J. Med.* 319:537–541; and Bugawan et al., 1988, *Bio/Technology* 6:943–947, each of which is incorporated herein by reference. Useful chromogens include red leuco dye and 3,3',5,5'-tetramethylbenzidine (TMB). Helmuth, *PCR Protocols*, San Diego, Calif., Academic Press, Inc., 1990, pp. 119–128, describes procedures for non-isotopic detection of PCR products and is incorporated herein by reference.

The probes of the invention can be used to determine if nucleic acid sequences are present in a sample by determining if the probes bind to the sequences present in the sample. Suitable assay methods for purposes of the present invention to detect hybrids formed between probes and nucleic acid sequences in a sample are known in the art. For example, the detection can be accomplished using a dot blot format, as described in the Example 4. In the dot blot format, the unlabeled amplified sample is bound to a solid support, such as a membrane, the membrane incubated with labeled probe under suitable hybridization conditions, the unhybridized probe removed by washing, and the filter monitored for the presence of bound probe. When multiple samples are analyzed with few probes, such as the case when samples are screened for the presence of mycobacterial nucleic acid using genus specific probes, the dot blot format is quite useful.

An alternate method is quite useful when large numbers of different probes are to be used. This method is a "reverse" dot blot, in which the amplified sequence contains a label, and the probe is bound to the solid support. In this format, the unlabeled probes are bound to the membrane and exposed to the labeled sample under appropriately stringent hybridization conditions. Unhybridized labeled sample is then removed by washing under suitably stringent conditions, and the filter is then monitored for the presence of bound sequences. Because species determination requires the use of multiple species specific probes for each amplified sample, the reverse dot blot format is the preferred test format for this step.

Alternatively, it may be desirable to use a detection method having a plurality of probe hybridization sites or wells. For example, a solid support such as a microtiter plate is particularly useful in large scale clinical applications of the present methods. Copending U.S. patent application Ser. Nos. 414,542 and 695,072, filed Nov. 20, 1991, May 3, 1991, respectively, and incorporated herein by reference, describe preferred methods for hybridization/capture of PCR amplified DNA or solid supports. In one embodiment of those methods the amplified target DNA is labeled (e.g., with biotin) during amplification in the PCR reaction. The labeled DNA is specifically captured by hybridization of PCR product to a target-specific oligonucleotide capture probe that has been bound to the microtiter plate well. The bound product is suitably detected according to the type of label used. For example, if biotin is used as a label, avidin HRP complex is added and is reacted with either (a) hydrogen peroxide substrate and O-phenylene diamine (OPD) chromogen or (b) hydrogen peroxide substrate and tetramethylbenzidine chromogen (TMB). A color metric signal develops, allowing for the quantitative detection of the PCR amplified DNA.

As practiced in clinical biomedical labs, detection procedures using microtiter plate assays can be standardized for a wide range of targets. It may be preferable to have detection probes less than 25 nucleotides in length. Shorter probes minimize opportunity for cross reactivity and are particularly helpful in large scale screening procedures. Accordingly, Example 8 a describes preferred method for detecting Mycobacterium species in a microtiter plate format. One skilled in the art would recognize that probes longer than 25 nucleotides are equally suitable for microtiter plate detection schemes; however, it may be necessary to individually determine the appropriate hybridization and stringency conditions to insure the maximum specificity.

Another suitable assay system is described in U.S. patent application Ser. No. 563,758, filed Aug. 6, 1990, incorporated herein by reference, in which a labeled probe is added during the PCR amplification process. Any probe that hybridizes to target DNA during each synthesis step is degraded by the 5' to 3' exonuclease activity of the polymerase used to catalyze primer extension. The degradation product from the probe is then detected. Thus, the presence of the degradation product indicates that the hybridization between the probe and the target DNA occurred.

The present invention also relates to kits, multicontainer units comprising the primers and probes of the invention. A useful kit can contain SSO probes for detecting mycobacterial nucleic acid. In some cases, the SSO probes may be fixed to an appropriate support membrane. The kit can also contain primers for PCR amplification. Other optional components of the kit include, for example, reverse-transcriptase or polymerase, the substrate nucleoside triphosphates, means used to label (for example, an avidin-enzyme conjugate and enzyme substrate and chromogen if the label is biotin) or detect label, and the appropriate buffers for PCR, reverse transcription, or hybridization reactions. In addition to the above components, the kit can also contain instructions for carrying out amplification and detection methods of the invention.

In a preferred embodiment of the invention, kits for detecting mycobacteria may also include positive and negative controls. Preferably a positive control includes a nucleic acid sequence that is amplifiable using the same primer pair used to amplify mycobacterial nucleic acids in a test sample. Methods for using a positive control, wherein both the target that may or may not be present, and the positive control, use the same primer pair are described in copending U.S. Pat. No. 5,219,727, filed Sep. 28, 1989, incorporated herein by reference. Preferably the positive control is designed so that the product DNA is of a discrete size readily distinguishable from the size of the target.

In another aspect, the present invention provides a positive control that is capable of hybridizing to probes for detecting genus-specific mycobacterium probes as well as species-specific mycobacterium probes. Example 9 describes the construction of a positive control nucleic acid.

As described herein, it may be desirable to utilize a second amplification target, particularly for resolving discordant PCR and culture data. Given the teaching of the present invention for providing an internal positive control vector, one of ordinary skill in the art would readily appreciate that additional internal positive controls could be constructed. For example, a positive control could incorporate primer sites for both the primary (16S rRNA) and secondary target (e.g., 65-kDa protein gene) to hybridize and subsequently amplify a discrete segment of positive control DNA.

The examples of the present invention presented below are provided only for illustrative purposes and not to limit the scope of the invention. Numerous embodiments of the invention within the scope of the claims that follow the examples will be apparent to those of ordinary skill in the art from reading the foregoing text and following examples.

EXAMPLE 1

Sample Preparation

Nucleic acids are isolated from sputum samples using the IsoQuick ™ system commercially available from MicroProbe. About 10 ml of a sputum sample is liquified/disinfected, pelleted by centrifugation, and resuspended in about 1 ml of buffer with BSA. From this sample, 200 to 500 $\mu$l are centrifuged to pellet the bacteria. The pellets are resuspended in 100 $\mu$l of sample buffer A, then lysed with 100 $\mu$l of lysis Reagent 1. Lysates are then extracted with 7 volumes of Reagents 2 and 4 volumes of Reagent 3 (Reagents 1, 2, and 3, along with sample buffer A, are supplied with the Iso- Quick ™ system). The sample is centrifuged and, afterwards, ⅓ volume of 10 M NH₄Ac is added to the aqueous phase and the DNA precipitated with an equal volume of isopropanol. The pelleted DNA is washed with 70% EtOH, air dried, and resuspended in 100 μl TE, pH 8.0. A 50 μl volume of each DNA preparation is used in the amplification reaction.

EXAMPLE 2

Amplification of Mycobacterial DNA

A master reagent mixture is prepared so that each reaction contains the following reagents: 25 pmol of each primer, 10 nmol of each dNTP, PCR buffer at 233 (10× buffer=500 mM KCL, 500 mM Tris-HCL, pH 8.9, 20 mM $MgCl_2$), 3 units of Taq polymerase (Perkin Elmer), 2 units of UNG (Perkin Elmer), and $H_2O$ to make 50 μl reaction mixture per reaction. This master mix is overlayed with 50 μl of mineral oil, and the DNA sample is added to the reaction mixture under the oil layer. As necessary, $H_2O$ is added to make up a total reaction volume of 100 μl.

The DNA is amplified in a Perkin Elmer Thermal Cycler. The Thermal Cycler is programmed to go through 37 cycles of denaturation, primer annealing, and primer extension; two cycles of 98° C., 62° C., and 72° C. for one minute each, followed by 35 cycles of 94° C., 62° C., and 72° C. for one minute each. The Perkin Elmer Thermal Cycler is programmed to soak the samples at 72° C. for an indeterminate time after the last cycle to ensure that the final extension is complete and to keep the UNG enzyme inactive, if the UNG sterilization system is used. The amplification products can then be analyzed by gel electrophoresis and/or dot blot hybridization. If analysis by gel electrophoresis is to be done, about 10 μl of 10× sample buffer (0.25% xylene cyanol, 0.25% bromophenol blue, 25% Ficoll) are added, and the mineral oil is extracted, and Taq polymerase is inactivated, with 100 μl of chloroform.

EXAMPLE 3

Dot Blot Format

The initial screening of the amplified sample detects the presence of Mycobacterium nucleic acid. In the dot blot format, a small portion of the amplified DNA is denatured, applied to a nylon filter, and immobilized as described below. The filter is then immersed in a probe solution to allow hybridization to one of the labelled probes. Each of the probes can be radioactively labelled, but probes covalently conjugated to horseradish peroxidase (HRP) can also be used to provide a means of nonisotopic detection in the presence of a chromogenic or chemiluminescent substrate. Immobilized target DNA is hybridized to a mixture of the two genus specific probes KY101 (SEQ ID NO: 3) and KY102 (SEQ ID NO: 4). Because the number of samples examined is expected to exceed greatly the number of probes (one mixture of two probes), the dot blot format is most convenient for this initial screening. A large number of different samples can be hybridized onto discrete locations of a single solid support and exposed to the labelled probes simultaneously by immersion of the support in a probe solution.

The amplification is carried out as in Example 2. The PCR product is then denatured by treatment with alkali. To 5 μl of PCR product is added 5 μl of 0.5M EDTA, pH 8.0, 8 μl of 5N NaOH, and 82 μl of $H_2O$.

The mixture is allowed to stand at room temperature for 10 minutes to complete denaturation.

BioDyne ™ B nylon filters (Pall Corp., Glen Cove, N.Y.) are prepared by soaking in $H_2O$ for 5 to 10 minutes and further rinsing with 200 μl of $H_2O$ after the dot-blot manifold (Bio-Dot ™ from Bio Rad, Richmond, Calif.) has been set up. Following denaturation, 100 μl of the sample mixture is applied under vacuum to the nylon membrane using the dot blot apparatus. Each well is then rinsed with 200 μl of 0.4N NaOH, then rinsed briefly with 2× SSC, and air dried until no pools of liquid are left. The DNA is immobilized and crosslinked to the nylon filter by ultraviolet irradiation at a flux of 1200 $mJ/cm^2$ with a Stratalinker ™ (Stratagene, La Jolla, Calif.) UV light box (at the "autocrosslink" setting).

Filters are "prehybridized" by soaking in the hybridization buffer (0.5× SSC, 5× Denhardt's solution, 0.1% SDS, 50 μg/ml of herring sperm DNA) in heat sealable bags at 60° C. (air shaker) for at least 30 minutes. If radioactively labeled probes are used, the buffer is then replaced with an equal amount of the same solution containing $1 \times 10^6$ cpm probe, and the filter is allowed to hybridize between 2 hours and overnight at 60° C.

After hybridization, filters are washed three times in 2× SSC/0.1% SDS; twice for 20 minutes at room temperature, and then once for twenty minutes at the high stringency temperature of 71° C. in a shaking water bath. The filters are then blotted dry, wrapped in plastic wrap, and exposed to X-ray film at −70° C. with one or two intensifying screens.

An alternate method of visualization is to hybridize with horseradish peroxidase conjugated oligonucleotide probes, prepared as described by Levenson and Chang, 1989, in *PCR Protocols: A Guide to Methods and Applications,* (Innis et at., eds., Academic Press. San Diego) pages 92–112, incorporated herein by reference, and Saiki et al., 1988, *N. Eng. J. Med.* 319:537–541. Hybridization is carried out with 2 pmoles of HRP-SSO probe per 5 ml of hybridization solution.

After washing, filters to be developed with a chromogenic dye substrate are rinsed in 100 mM sodium citrate, pH 5.0, then placed in 100 mM sodium citrate, pH 5.0, containing 0.1 mg/ml of 3,3',5,5'-tetramethylbenzidine per milliliter (Fluka) and 0.0015 percent hydrogen peroxide, and incubated with gentle agitation for 10 to 30 minutes at room temperature. Developed filters are rinsed in water and immediately photographed. The TMB detection system is prepared and used substantially as described in AmpliType ® DQalpha DNA typing kit developed and manufactured by Hoffmann-La Roche and available through Perkin Elmer. In another embodiment, filters are developed with the chemiluminescent detection system (ECL; Amersham, Arlington Heights, Ill.). Filters are rinsed in PBS for 5 minutes and placed in the ECL solution for 1 minute with gentle agitation. Filters are then exposed to X-ray film at room temperature for 1 to 5 minutes.

EXAMPLE 4

Reverse Dot Blot Format

Species identification requires that each sample be exposed to a variety of species specific probes: the identity is indicated by which of the probes bind to the sample DNA. Because each sample is exposed to multiple probes, the reverse dot blot format is more convenient. The probes are fixed to discrete locations on a membrane and then the entire membrane is immersed in a solution containing the amplified target DNA to allow hybridization to the membrane-bound probes. The reverse dot blot process is described in copending application Ser. Nos. 197,000 and 347,495; in Saiki et al., 1989, *Proc. Natl. Acad. Sci.* 86:6230–6234; and in the AmpliType ® DQalpha DNA typing kit developed and manufactured by Hoffmann-La Roche and available through Perkin Elmer, each of which is incorporated herein by reference. The amplification primers are biotinylated, as described in Levenson and Chang, 1989, supra, so that any amplified DNA that hybridizes to the membrane bound probes can be easily detected.

In one embodiment, detection is carried out by reacting streptavidin conjugated horseradish peroxidase (SA-HRP) with any biotinylated (through the primers), amplified DNA hybridized to the membrane-bound probe. The HRP thus becomes bound, through the SA-biotin interaction, to the amplified DNA and can be used to generate a signal by a variety of well known means, such as the generation of a colored compound, e.g., by the oxidation of tetramethylbenzidine (see U.S. Pat. No. 4,789,630, incorporated herein by reference).

Although the probe can be fixed to the membrane by any means, a preferred method involves "tailing" all oligonucleotide probe's hybridizing region with a much longer sequence of poly-dT. The resulting poly-dT "tail" can then be reacted with amine groups on a nylon membrane to fix the probe covalently to the membrane. This reaction can be facilitated by UV irradiation.

Terminal deoxyribonucleotidyl transferase (TdT, Ratliff Biochemicals; for the reactions below assume a concentration of abut 120 Units/µl, which is 100 pmole/µl) can be used to create a poly-dT tail on a probe, although one can also synthesize the tailed probe on a commercially available DNA synthesizer. When one uses a DNA synthesizer to make the tailed probe, however, one should place the tail on the 5' end of the probe, so that undesired premature chain termination occurs primarily in the tail region.

TdT reactions should be carried out in a volume of about 100 µl containing 1× TdT salts, 200 pmole of oligonucleotide, 800 µM DTT, and 60 units of TdT. 10× TdT salts is 1,000 mM K-cacodylate, 10 mM COCl$_2$, 2 mM dithiothreitol, 250 mM Tris-Cl, pH 7.6, and is prepared as described by Roychoudhury and Wu, *Meth. Enzymol.* 65: 43–62, incorporated herein by reference. A 10× stock solution of 8 mM dTTP can be prepared (neutralized to pH 7 with NaOH) for convenience.

The TdT reaction should be carried out at 37° C. for two hours and then stopped by the addition of 100 µl of 10 mM EDTA, pH 8. The final concentration of tailed oligonucleotide is 1 µM (1 pmole/µl), and the length of the homopolymer tail is about 400 residues. Tail length can be changed by adjusting the molar ratio of dTTP to oligonucleotide. The tailed probes can be stored at −20° C. until use.

The nylon membrane preferred for the reverse dot blot format is the Biodyne ™ B nylon membrane, 0.45 micron pore size, manufactured by Pall and also marketed by ICN as the BioTrans ™ nylon membrane. The probes can be spotted onto the membrane very conveniently with the Bio-Dot ™ dot blot apparatus manufactured by BioRad. Each probe is spotted onto a unique, discrete location on the membrane. About 2 to 10 picomoles of each tailed probe is premixed with 50 to 100 µl of TE buffer before application to the dot blot apparatus. After dot blotting, the membrane is briefly placed on absorbent paper to draw off excess liquid. The membrane is then placed inside a UV light box, such as the Stratalinker ™ light box manufactured by Stratagene, and exposed to 50 to 60 millijoules/cm$^2$ of flux at 254 nm to fix the tailed probe to the nylon membrane. After a brief rinse (for about 15 minutes in hybridization solution) to remove unbound probe, the membrane is then ready for hybridization with biotinylated PCR product.

Amplified PCR products are denatured by heating to 95° C. for 3 to 10 minutes, and 40 µl of the denatured PCR product are added to each probe panel for hybridization. Hybridization is carried out at 57° C. for 20 minutes in a shaking water bath in a hybridization buffer composed of 0.5× SSC, 0.25% SDS, and 5× Denhardt's solution. The hybridization buffer is replaced with 3 ml of a solution consisting of 25 µl of SA-HRP, commercially available from Perkin Elmer, in 3.1 ml of hybridization buffer, and incubated for 20 minutes at 57° C. in a shaking water bath.

Washing is carried out in a wash buffer of 2× SSC and 0.1% SDS. After a brief rinse of the membrane in 10 ml of wash buffer, a 12 minute stringent wash in 10 ml of buffer is done at 57° C. Another 5 minute room temperature wash is then carried out, followed by a 5 minute wash in 10 ml of 0.1M sodium citrate, pH 5.0.

Chromogen binding is carried out in 5 ml of chromogen solution consisting of 5 ml of 0.1M sodium citrate, 5 µl of 3% hydrogen peroxide, and 0.25 ml of chromogen (TMB from Perkin Elmer) for 25–30 minutes at room temperature. Three 10 minute washes in distilled water are carried out at room temperature. A post-wash of 1× PBS at room temperature for 30 minutes can enhance signal quality. During steps in which chromogen is present, the membrane should be shielded from light by an aluminum foil covering. The developed membrane should be photographed for a permanent record.

EXAMPLE 5

Mycobacterial DNA Detection

Detection of mycobacterial DNA was accomplished by amplification with biotinylated forms of the genus specific primers KY18 (SEQ ID NO: 1) and KY75 (SEQ ID NO: 2), using the protocol described in Example 2, above, followed by hybridization to the genus specific probes KY101 (SEQ ID NO: 3) and KY102 (SEQ ID NO: 4), using the dot blot assay described in Example 3, above. The sequences of the hybridizing regions of the upstream primer KY18 (SEQ ID NO: 1) and the downstream primer KY75 (SEQ ID NO: 2) are given in Table 1, above. The sequences of the hybridizing regions of the genus-specific probes KY101 (SEQ ID NO: 3) and KY102 (SEQ ID NO: 4) are given in Table 2, above.

The genus specific primers KY18 (SEQ ID NO. 1) and KY75 (SEQ ID NO. 2) were used in polymerase chain reaction (PCR) amplifications to amplify nucleic acid from 15 Mycobacterium species. The results are shown in Table 4. As expected, KY18 (SEQ ID NO. 1)/KY75 (SEQ ID NO. 2) amplified DNA from all Mycobacterium species except *M. simiae*. Amplification of *M. simiae* or *M. chitae* DNA was not expected because KY75 (SEQ ID NO. 2) differs in four of the five 3'-terminal bases from *M. simiae* and in two of the 3'-terminal bases from *M. chitae*. However, because the association of *M. simiae* with human disease has rarely been reported, detection is not clinically important. With the exception of DNA from *M. xenopi* and *M. terrae*, all amplified mycobacterial DNA hybridized was detected by hybridization to the genus specific probes KY101 (SEQ ID NO. 3) and KY102 (SEQ ID NO. 4).

TABLE 4

Amplificafion of DNA from Different Mycobacterial Species and Hybridization to Genus SDecific Probes

| Mycobacteria | Amplification | Hybridization |
|---|---|---|
| M. tuberculosis | + | + |
| M. scrofulaceum | + | + |
| M. fortuitum | + | + |
| M. avium | + | + |
| M. kansasii | + | + |
| M. intracellulare | + | + |
| M. phlei | + | + |
| M. smegmatis | + | + |
| M. marinum | + | + |
| M. favescens | + | + |
| M. xenopi | + | − |
| M. simiae | − | − |
| M. chelonae | + | + |
| M. gordonae | + | + |
| M. terrae | + | − |

The specificity of these primers was tested by attempting to amplify DNA from 22 different non-mycobacterial species. Amplification products resulted only from the DNA of *Corynebacter diptheriae* and *Corynebacter xerosis*, *Nisseria sicca*, and *Propionibacterium acnes*. However, these amplification products failed to hybridize with the genus specific probes, so no false positives resulted. The organisms tested are listed in Table 5, below.

TABLE 5

| Amplification of DNA from Non-Mycobacterial Organisms | | |
|---|---|---|
| Organism | amplification | Hybridization |
| Bordatella pertussis | − | − |
| Borrelia burgdorferi | − | − |
| Corynebacter diphtheriae | + | − |
| Corynebacter xerosis | + | − |
| Enterobacter aerogenes | − | − |
| Escherichia coli | − | − |
| Haemophilus influenzae | − | − |
| Klebsiella pneumoniae | − | − |
| Legionella pneumophila | − | − |
| Neisseria gonorrhea | − | − |
| Neisseria meningitidis | − | − |
| Nisseria sicca | + | − |
| Propionibacterium acnes | + | − |
| Psuedomonas aeruginosa | − | − |
| Salmonella typhimurium | − | − |
| Serratia marcescens | − | − |
| Staphylococcus aureus | − | − |
| Streptococcus agalactiae | − | − |
| Streptococcus pyogenes | − | − |
| Streptomyces hygrocopicus | − | − |
| Streptomyces rubiginosis | − | − |
| Treponema pallidum | − | − |

EXAMPLE 6

Species Identification

Once mycobacterial nucleic acid has been detected in a clinical sample, the species from which the nucleic acid originates can be determined by the pattern of hybridization with the species specific probes using the reverse dot blot format of Example 4. The species of clinical interest to be detected by the present system are *M. avium*, *M. intracellulare*, *M. kansasii*, and *M. tuberculosis*. In addition, detection of *M. gordonae* is desired because that organism is frequently found in clinical samples.

FIG. 1 shows the results of a test of the specificity of species specific probes selected from the probes listed in Table 3. The sequence of the hybridizing region of each probe, along with the expected specificity, is shown in Table 3, above. Amplified products from purified DNA from thirteen different species of Mycobacterium were used to test the specificity of both the genus specific and species specific probes. For each species, 1 pg of DNA purified from cultured bacteria (the equivalent of about 300 bacterial genomes) was amplified as in Example 2 using biotinylated primers. Detection of probe hybridization was done using the reverse dot-blot format of Example 4. As a positive control for the presence of amplified DNA, the genus specific probes were included on the test strips along with the species specific probes.

EXAMPLE 7

Amplification of Mycobacterial 16S rRNA

The 16S rRNA can be amplified by first creating cDNA by reverse transcription and amplifying the cDNA. The same primers are used as in Example 2, above. In this example, both the high temperature reverse transcription and the PCR amplification are carried out with the thermostable Tth polymerase.

The reverse transcription is carried out in a volume of 20 μl containing the following components: 8 μl of H$_2$O, 2 μl of 10× RT reaction buffer (100 mM Tris-HCL, pH 8.3, and 900 mM KCL), 2 μl of 10 mM MnCl$_2$, 2 μl of dNTP solution (2 mM each of dATP, dCTP, dGTP, and dTTP in H$_2$O, pH 7.0), 2 μl of the "downstream" primer (7.5 mM in H$_2$O), 2 μl of 0.18 μM Tth polymerase in 1× storage buffer (20 mM Tris-HCL, pH 7.5, 100 mM KCL, 0.1 mM EDTA, 1 mM DTT, 0.2% Tween 20 (Pierce Surfactants), 50% (volume/volume) glycerol), and 2 μl of template RNA solution (<250 ng in 10 mM Tris-HCL and 1 mM EDTA). All solutions not containing Tris are treated with diethylpyrocarbonate (DEPC) to remove any contaminating ribonuclease as described on page 190 of Maniatus et al., 1982, *Molecular Cloning, a Laboratory Manual* (Cold Springs Harbor Laboratory, New York). The reverse transcription is carried out at 72° C. for 5 minutes in a thermocycler. The reaction is stopped by cooling the reaction to 4° C. with ice.

The PCR amplification is performed with the following reagents added: 2 μl of the remaining primer (7.5 mM in H$_2$O), 2 μl of dNTP solution (10 mM each of dATP, dCTP, dGTP, and dTTP in H$_2$O, pH 7.0), 8 μl of 10× PCR reaction buffer (100 mM Tris-HCL, pH 8.3, 1 mM KCL, 18.75 mM MgCl$_2$, 7.5 mM EGTA, and 50% (volume/volume) glycerol), and 68 μl DEPC treated H$_2$O. The nucleic acid is amplified in a Perkin Elmer Thermal Cycler with the same thermal profile as in Example 2. The amplified product is analyzed as in the prior examples.

EXAMPLE 8

Microtiter Plate Assay for the Detection of Mycobacterium

In this embodiment of the invention, the probe is fixed to a well of a microtiter plate. The amplified target DNA is hybridized to the bound probe as described above. As in the previous example, the amplification primers are biotinylated to allow detection of amplified DNA that hybridizes to the bound probes.

The desired probes, conjugated to BSA, were first allowed to adsorb to the plastic surface of the individual wells. The wells were then blocked with protein, such as bovine serum albumin. Preferably, 96 well plates available from Corning are used.

Once the amplification has been completed, the PCR tubes were removed from the thermocycler (available through Perkin Elmer). One hundred microliters of denaturation solution were added to each PCR tube. A new pipette tip is used for each tube. In one embodiment, detection may not be preformed immediately. In that case, the PCR tubes were storied overnight at 2° C. to 8° C. Denatured amplification reactions become viscus upon storage at 2° C. to 8° C. Tubes were briefly warmed at 25° C. to 30° C. prior to opening tubes to make pipette easy.

The appropriate number of eight well microtiter plate strips (minimally 2 strips) were removed and set into the microtiter plate frame. One hundred microliters of hybridization buffer was pipetted into each well of the microtiter plate.

The denaturation solution contains 0.4M NaOH; 80 mM EDTA and 0.005% Thymol blue. Hybridization/neutralization buffer contains: 3M NaSCN; 80 mM $NaH_2PO_4$; 10 mM $NaH_2PO_4$; and 0.125% Tween 20. Before use the pH is checked to be 5.0±0.2.

Using plugged tips with a multi channel pipetter, 25 μl of the denatured amplification reaction from each PCR tube in the tray was pipetted to the corresponding well position in the microtiter plate. The plate was covered with the microtiter plate lid and gently tapped on the side 10 to 15 times. Wells in which proper reagent pipeting has been done will turn light yellow in color. If no or only a single change in blue color is noted, excess amplicon has been added. The test is continued as positive OD values will increase but negative OD values are not affected. The plate was incubated for 60 minutes at 37° C. After the initial hybridization at 37° C. for one hour, the hybridization/neutralization buffer was removed and replaced with the same buffer and the plate was incubated for an additional 15 minutes at 37° C.

Following incubation the plate was washed five times with wash solution. Washing of the plate may be preformed manually or with an automated microtiter plate washer programmed accordingly. For washing, a 1× PCR wash buffer was used. A 10× concentrate of PCR washed buffer was prepared as follows: 9.94 grams per liter of sodium phosphate dibasic; 4.41 grams per liter sodium phosphate (monobasic); 3.722 grams per liter EDTA; 87.66 grams per liter sodium chloride; 13.7 grams per liter of Tween 20; and 10 grams per liter of Pro Clin 300 (Rohm and Haas, Philadelphia, Pa.). The solution is pit with phosphoric acid (pH 6.5–7.1 is preferred).

For manual washing the contents of the plate were emptied and tapped dry. Three hundred microliters of wash solution was added to each well in the plate being tested, and the plate was allowed to dry for 15 to 30 seconds. The plate was again emptied and tapped dry. This wash process was repeated four additional times.

For an automated microplate washer, the following procedure was used. The contents of the wells was aspirated. The washer was programmed to add 350 microliters of working wash solution to each well in the plate being tested and soaked for 30 seconds and aspirated. The steps were repeated four additional times. The plate was then tapped dry.

One hundred microliters of conjugate was added to each well in the plate being tested. The avidin-HRP conjugate is prepared as follows. The diluent contains 0.1 molar; 0.25% Emulsit 25 (DKS International, Inc., Tokyo, Japan); 1.0% Kathon CG (Rohm and Haas, Philadelphia, Pa.); 0.1% phenol; 1.0% bovine gamma globulin. The solution was pH to 7.3 with concentrated HCl. To this diluent 10 nM of conjugated avidin (Vector Labs, Burlingame, Calif.) was added. The plate was then covered and then incubated 50 minutes at 37° C. and again washed as described above. The working substrate was prepared by mixing 2.0 ml of Substrate A and 0.5 ml of Substrate B for each multiple of two 8 well microtiter plate strips (16 tests). Substrate A contains 3 mM hydrogen peroxide, 6.5 mM citrate and 0.1% Kathon CG. Substrate B contains 4.2 mM 3,3',5,5' tetramethylbenzidine and 40% dimethylformamide. The working substrate was prepared no more than three hours before use and was stored away from direct sunlight.

One hundred microliters of working substrate (substrate A and B mixture) was added to each well of the plate being tested. The plate was then covered and incubated in the dark for 10 minutes at room temperature (20° C. to 25° C.). One hundred microliters of Stop Reagent (5% $H_2SO_4$) was added to each well being tested. The absorbance of each well of 450 nM was read within one hour of adding the Stop Reagent. The absorbance value was recorded for specimen and control.

EXAMPLE 9

The Construction of a Positive Control Vector Useful in Methods for the Amplification and Detection of Mycrobacterial Nucleic Acids Oligonucleotides which contain the species-specific probe binding sequences as well as their complements (KY178 [SEQ ID NO. 24]–KY181 [SEQ ID NO. 27] below) were synthesized. (These oligos contain recognition sites for restriction enzymes at both termini to facilitate cloning.) One microgram each of KY178 (SEQ ID NO. 24) and KY179 (SEQ ID NO. 25) or KY180 (SEQ ID NO. 26) and KY181 (SEQ ID NO. 27) were combined, heated for 5 minutes at 98° C. then incubated for one hour at 75° C. to allow annealing of the complementary strands. Annealed products were separated from residual single-stranded oligos by electrophoresis through 3% Nusieve (FMC Products)/1% agarose gel. The bands of double-stranded products are cut out and the DNA eluted. The DNA fragments are then cut with the appropriate restriction enzymes and ligated to each other. The ligation products are isolated from Nusieve/agarose gel as above.

The recipient vector was prepared. The recipient vector was a plasmid into which a fragment of the *M. tb* 16S rRNA gene containing the primer and probe binding sites have been inserted and was prepared as follows.

Fifty picograms of *M. tuberculosis* DNA was amplified using primers KY70 (SEQ ID NO. 28) and CR01 (SEQ ID NO. 29) in the presence of 50 pmol CR01 (SEQ ID NO. 29), 80 pmol KY70 (SEQ ID NO. 28), 20 nmol of each dNTP, 2.5 units Taq polymerase, and 1× PCR buffer (50 mM Tris-HCl, pH 8.9; 50 mM KCl; 1.5 mM $MgCl_2$) in a total reaction volume of 100 microliters. Thermal cycling conditions are as outlined in Example 2. The amplification products were extracted with 100 microliters chloroform.

The amplification products and vector pBS(+) (Stratagene) were both digested with restriction endonuclease Pst I, extracted once with phenol/chloroform, and then precipitated with ethanol. (CRO1 contains a Pst I site at the 5'-end and the amplification product contains an internal Pst I site downstream of the binding sites for the mycobacteria-specific primers and probes.) The Pst I cut vector was dephosphorylated by treatment with calf intestine phosphatase (Maniatis), extracted with phenol/chloroform, and precipitated with ethanol. The prepared amplification products were ligated to the vector under standard condition (Maniatis).

The ligated DNA were transformed into competent E. coli. Colonies carrying plasmids that contain the desired insert were identified by colony blot hybridization to the tb-specific probe KY21 (SEQ ID NO. 5) as follows. Bacteria were streaked onto a nitrocellulose filter disk overlaid onto a nutrient agar plate and allowed to grow overnight. The filter was removed and successively overlaid (bacteria-side up) onto 3 MM filter papers soaked with 10% SDS (3 minutes), 0.5M NaOH/1.5M NaCl (5 minutes), 0.5M Tris-HCl, pH8/1.5M NaCl (5 minutes), and 2× SSC (5 minutes). The filters were air-dried. The DNA were cross-linked onto the filter by UV irradiation and then hybridized to KY21 (SEQ ID NO. 5) and washed as outlined in Example 3.

Oligonucleotide Sequences:
KY70 SEQ ID NO. 28
   GCGGTACCTG CACACAGGCC ACAAGGGAA
CR01 SEQ ID NO. 29
   CGCCTGCAGT TAACACATGC AAGTCGAACG G This vector, designated pKY5, was cut with the restriction enzymes Sty I and Xho I to remove a 174 bp fragment containing the species-specific probe binding site but leaving intact the primer and genus-specific probe binding sites. The cut plasmid was separated from the 174 bp fragment by electrophoresis through 1.5% low melting temperature agarose gel. The band containing the vector was cut from the gel and purified by chromatography through a NACS column (Bethesda Research Lab) and ethanol precipitation. The insert fragment containing recognition sites for the species-specific probes is ligated to the prepared vector. The ligation products are transformed into competent host bacteria.

Transformants containing the appropriate inserts are identified by PCR amplification. Transformant bacterial colonies are resuspended in 0.5 ml TE buffer. Fifty microliters of the bacterial suspension are placed in PCR reaction tubes containing components necessary for amplification of mycobacterial DNA and amplification is carried as discussed above. Bacteria which carry plasmids containing the desired insert will generate PCR products of 640 bp using primer pair KY18 (SEQ ID NO. 1) and KY75 (SEQ ID NO. 2). Amplification of bacteria containing the original pKY5 plasmid generates PCR products of 584 bp.

The amplicons thus generated can be hybridized to mycobacterial genus-specific and species-specific probes by reverse dot-blot hybridization as outlined in Example 4 to confirm the presence of the hybridization sites for the genus-specific and species-specific probes described in the Examples. Positive control plasmid can be similarly prepared for hybridizing to genus probes and a select subset of species specific probes. In a kit format, for example, it may be desirable to include a positive control plasmid for distinguishing tuberculosis from other species, in addition to including a positive control plasmid containing sequences KY178–KY181 (SEQ ID NOS. 24–27).

Oligonucleotide sequences:

| KY178 - SEQ. ID NO. 24 | | | | |
|---|---|---|---|---|
| 5' CCATCGATAG | GACCATTCTG | CGCATGTGGT | GTGGTGGGTC | TAATACCGAA |
| TAGGACCACA | GGACACATGA | AGGCTCACTT | TGTGGGTTGA | CGGTAGGTAA |
| CACTTGGCGC | ATGCCTTGTG | GTGGAAAGCT | TCCAAGGCA 3' | |
| KY179 - SEQ. ID NO. 25 | | | | |
| 5' TGCCTTGGAA | GCTTTCCACC | ACAAGGCATG | CGCCAAGTGT | TACCTACCGT |
| CAACCCACAA | AGTGAGCCTT | CATGTGTCCT | GTGGTCCTAT | TCGGTATTAG |
| ACCCACCACA | CCACATGCGC | AGAATGGTCC | TATCGATGG 3' | |
| KY180 - SEQ. ID NO. 26 | | | | |
| 5' CCGCTCGAGA | CGGGATGCAT | GTCTTGTGGT | GGAAAGCGCT | TTAGCGGTAA |
| CTTTAGGCGC | ATGTCTTTAG | GTGGAAAGCT | TAACTCAAGA | CGCATGTCTT |
| CTGGTGGAAA | GCTTTTGCAT | CGATGG 3' | | |
| KY181 - SEQ. ID NO. 27 | | | | |
| 5' CCATCGATGC | AAAAGCTTTC | CACCAGAAGA | CATGCGTCTT | GAGTTAAGCT |
| TTCCACCTAA | AGACATGCC | CTAAAGTTAC | CGCTAAAGCG | CTTTCCACCA |
| CAAGACATGC | ATCCCGTCTC | GAGCGG 3' | | |

EXAMPLE 10

The Use of Positive Control Plasmid

One use of the positive control plasmid is to monitor the efficiency of amplification in any specific experiment. In such applications, serial dilutions of the positive control plasmid are made. Known copy numbers of the plasmid can be used as templates in amplification reactions. The lowest number of plasmid DNA molecules that can be amplified gives a measurement of the efficiency of the amplification reaction. Another use of the positive control plasmid is to generate products which can be used to monitor the efficiency with which the genus and species-specific probes detects mycobacterial DNA. Amplification products generated as above can serve as substrate in hybridization reaction. Generation of the appropriate hybridization signals allows for an assessment of how well the probes are able to detect mycobacterial DNA.

We claim:

1. A pair of oligonucleotide primers for amplifying a target region of the 16S ribosomal RNA gone or the corresponding RNA of a mycobacterial species, wherein the first primer is KY18 (SEQ ID NO. 1) and the second primer is KY75 (SEQ ID NO. 2).

2. An oligonucleotide probe for detecting 16S ribosomal RNA nucleic acid from a mycobacterial species, wherein said probe is selected from the group consisting of KY101 (SEQ ID NO. 3), KY102 (SEQ ID NO. 4), KY165 (SEQ ID NO. 13), KY166 (SEQ ID NO. 14), and sequences fully complementary thereto.

3. An oligonucleotide probe of claim 2 that is KY101 (SEQ ID NO. 3) or the sequence fully complementary thereto.

4. An oligonucleotide probe of claim 2 that is KY102 (SEQ ID NO. 4) or the sequence fully complementary thereof.

5. An oligonucleotide probe of claim 2 that is KY165 (SEQ ID NO. 13) or the sequence fully complementary thereto.

6. An oligonucleotide probe of claim 2 that is KY166 (SEQ ID NO. 14) or the sequence fully complementary thereto.

7. An oligonucleotide probe of claim 2 that is KY172 (SEQ ID NO. 22) or the sequence fully complementary thereto.

8. A kit for detecting and identifying a mycobacterial nucleic acid in a sample, said kit comprising a pair of primers, wherein the first primer is KY18 (SEQ ID NO. 1), and the second primer is KY75 (SEQ ID NO. 2).

9. The kit of claim 8, further comprising an oligonucleotide probe, wherein said probe is selected from the group consisting of KY101 (SEQ ID NO. 3), KY102 (SEQ ID NO. 4). KY165 (SEQ ID NO. 13), KY166 (SEQ ID NO. 14), and sequences complementary thereto.

10. The kit of claim 8, further comprising at least one oligonucleotide probe selected from the group consisting of KY21 (SEQ ID NO. 5), KY25 (SEQ ID NO. 6), KY26 (SEQ ID NO. 7), KY63 (SEQ ID NO. 8), KY151 (SEQ ID NO. 9), KY106 (SEQ ID NO. 10), KY126 (SEQ ID NO. 11), KY139 (SEQ ID NO. 12), KY157 (SEQ ID NO. 16), KY167 (SEQ ID NO. 17), KY168 (SEQ ID NO. 18), KY169 (SEQ ID NO. 19), KY170 (SEQ ID NO. 20), KY171 (SEQ ID NO. 21), KY172 (SEQ ID NO. 22), KY173 (SEQ ID NO. 23), and sequences complementary thereto.

11. The kit of claim 8, further comprising a panel of oligonucleotide probes comprising at least two oligonucleotide probes selected from the group consisting of KY21 (SEQ ID NO. 5), KY25 (SEQ ID NO. 6), KY26 (SEQ ID NO. 7), KY63 (SEQ ID NO. 8), KY151 (SEQ ID NO. 9), KY106 (SEQ ID NO. 10), KY126 (SEQ ID NO. 11), KY139 (SEQ ID NO. 12), KY157 (SEQ ID NO. 16), KY167 (SEQ ID NO. 17), KY168 (SEQ ID NO. 18), KY169 (SEQ ID NO. 19), KY170 (SEQ ID NO. 20), KY171 (SEQ ID NO. 21), KY172 (SEQ ID NO. 22), KY173 (SEQ ID NO. 23), and sequences fully complementary thereto.

12. The kit according to claim 8, further comprising a positive internal control oligonucleotide comprising an upstream primer hybridization site and a downstream primer hybridization site wherein said hybridization sites are complementary to the primers KY18 (SEQ ID NO. 1) and KY75 (SEQ ID NO. 2).

13. An internal positive control oligonucleotide sequence comprising an upstream primer hybridization site and a downstream primer hybridization site wherein said hybridization sites are complementary to the primers KY18 (SEQ ID NO. 1) and KY75 (SEQ ID NO. 2), and wherein said primer hybridization sites flank an oligonucleotide subsequence such that said oligonucleotide subsequence is amplified by a polymerase chain reaction using said primers.

14. The internal positive control oligonucleotide sequence of claim 13, wherein said subsequence further comprises a nucleic acid subsequence selected from the group consisting of KY101 (SEQ ID NO. 3), KY102 (SEQ ID NO. 4), KY165 (SEQ ID NO. 13), KY166 (SEQ ID NO. 14), and the sequences fully complementary thereto.

15. The internal positive control oligonucleotide sequence of claim 14, wherein said subsequence further comprises a nucleic acid subsequence selected from the group consisting of KY21(SEQ ID NO. 5), KY25 (SEQ ID NO. 6), KY26 (SEQ ID NO. 7), KY63 (SEQ ID NO. 8), KY151 (SEQ ID NO. 9), KY106 (SEQ ID NO. 10), KY126 (SEQ ID NO. 11), KY139 (SEQ ID NO. 12), KY157 (SEQ ID NO. 16), KY167 (SEQ ID NO. 17), KY168 (SEQ ID NO. 18), KY169 (SEQ ID NO. 19), KY170 (SEQ ID NO. 20), KY171 (SEQ ID NO. 21), KY172 (SEQ ID NO. 22), KY173 (SEQ ID NO. 23), and the sequences complementary thereto.

16. An oligonucleotide probe for detecting 16S ribosomal RNA nucleic acid from a mycobacterial species, wherein said probe is selected from the group consisting of KY21 (SEQ ID NO. 5), KY25 (SEQ ID NO. 6), KY26 (SEQ ID NO. 7), KY63 (SEQ ID NO. 8), KY151 (SEQ ID NO. 9), KY106 (SEQ ID NO. 10), KY126 (SEQ ID NO. 11), KY139 (SEQ ID NO. 12),KY157 (SEQ ID NO. 16), KY167 (SEQ ID NO. 17), KY168 (SEQ ID NO. 18), KY169 (SEQ ID NO. 19), KY170 (SEQ ID NO. 20), KY171 (SEQ ID NO. 21), KY172 (SEQ ID NO. 22), KY173 (SEQ ID NO. 23), and sequences fully complementary thereto.

17. A process for detecting mycobacterial nucleic acid contained in a sample, said process comprising:
(a) amplifying a region of said nucleic acid from a 16S ribosomal RNA gene, wherein the amplification is achieved by a polymerase chain reaction using a pair of primers consisting of the sequences KY18 (SEQ ID NO. 1) and KY75 (SEQ ID NO. 2);
(b) mixing said nucleic acid amplified in step (a) with an oligonucleotide probe selected from the group consisting of KY101 (SEQ ID NO. 3), KY102 (SEQ ID NO. 4), KY165 (SEQ ID NO. 13), KY166 (SEQ ID NO. 14), KY21 (SEQ ID NO. 5), KY25 (SEQ ID NO. 6), KY26 (SEQ ID NO. 7), KY63 (SEQ ID NO. 8), KY151 (SEQ ID NO. 9), KY106 (SEQ ID NO. 10), KY126 (SEQ ID NO, 11), KY139 (SEQ ID NO. 12), KY157 (SEQ ID NO. 16), KY167 (SEQ ID NO. 17). KY168 (SEQ ID NO. 18), KY169 (SEQ ID NO. 19), KY170 (SEQ ID NO. 20), KY171 (SEQ ID NO. 21), KY172 (SEQ ID NO. 22), KY173 (SEQ ID NO. 23), and sequences fully complementary thereto; and
(c) detecting hybrids formed between said nucleic acid and said probe.

18. A process for classifying a mycobacterium, said process comprising:
(a) amplifying a region of nucleic acid from a 16S ribosomal RNA gene from said mycobacterium, wherein the amplification is achieved by a polymerase chain reaction using a pair of primers consisting of the sequences KY18 (SEQ ID NO. 1) and KY75 (SEQ ID NO. 2);
(b) mixing said nucleic acid amplified in step (a) with a panel of sequence-specific oligonucleotide probes comprising at least two oligonucleotide probes selected from the group consisting of KY21 (SEQ ID NO. 5), KY25 (SEQ ID NO. 6), KY26 (SEQ ID NO. 7), KY63 (SEQ ID NO. 8), KY151 (SEQ ID NO. 9), KY106 (SEQ ID NO. 10), KY126 (SEQ ID NO. 11), KY139 (SEQ ID NO. 12), KY157 (SEQ ID NO. 16), KY167 (SEQ ID NO. 17), KY168 (SEQ ID NO. 18), KY169 (SEQ ID NO. 19), KY170 (SEQ ID NO. 20), KY171 (SEQ ID NO. 21), KY172 (SEQ ID NO. 22), KY173 (SEQ ID NO. 23), and sequences fully complementary thereto; and
(c) detecting hybrids formed between said nucleic acid and said probes.

* * * * *

UNITED STATES PATENT AND TRADEMARK OFFICE
CERTIFICATE OF CORRECTION

PATENT NO. : 5,422,242
DATED : June 6, 1995
INVENTOR(S) : Karen K.Y. Young It is certified that error appears in the above-identified patent and that said Letters Patent is hereby corrected as shown below:

In column 1, line 24, please delete "ADS" and insert therefor --AIDS--.

In column 1, line 59, please delete "hits" and insert therefor --has--.

In columns 7 and 8, Table 3, on the line beginning with "KY21" please delete "*tuberculosilis*" and insert therefor --*tuberculosis*--.

In columns 7 and 8, Table 3, on the line beginning with "KY63" please delete "*maringum*" and insert therefor --*marinum*--.

In columns 7 and 8, Table 3, on the line directly below the line beginning with "KY63" please delete "5' TCAAGACGCATGTTCTTCTGGTGGAAAGCTTTTGC 3'" and insert therefor --5' TCAAGACGCATGTCTTCTGGTGGAAAGCTTTTGC 3'--.

In column 10, line 35, please delete "file" and insert therefor --the--.

In column 14, line 59, please delete "IsoQuick TM" and insert therefor --IsoQuick™--.

In column 15, line 1, please delete "Quick TM" and insert therefor --Quick™--.

In column 15, line 14, please delete "233" and insert therefor --2X--.

In column 16, line 3, please delete "BioDyneTM" and insert therefor --BioDyne™--.

In column 16, line 14, please delete "StratalinkerTM" and insert therefor --Stratalinker™--.

In column 17, line 60, please delete "Biodyne TM" and insert therefor --Biodyne™--.

In column 17, line 62, please delete "BioTrans TM" and insert therefor --BioTrans™--.

In column 17, line 64, please delete "Bio-Dot TM" and insert therefor --Bio-Dot™--.

UNITED STATES PATENT AND TRADEMARK OFFICE
CERTIFICATE OF CORRECTION

PATENT NO. : 5,422,242

DATED : June 6, 1995

INVENTOR(S) : Karen K.Y. Young

It is certified that error appears in the above-identified patent and that said Letters Patent is hereby corrected as shown below:

In column 18, line 4, please delete "StratalinkerTM" and insert therefor --Stratalinker™--.

In column 19, line 9, please delete "SDecific" and insert therefor --Specific--.

In column 21, line 56, please delete "pit" and insert therefor --pH--.

In column 22, line 27, please delete "H2SO4" and insert therefor --$H_2SO_4$--.

In columns 23 and 24, line 2 of SEQ. ID NO. 25, please delete "AGTGAGCCIT" and insert therefor --AGTGAGCCTT--.

In column 35, Claim 1, line 44, please delete "gone" and insert therefor --gene--.

In column 35, Claim 7, line 66, please delete "2" and insert therefor --16--.

In column 36, Claim 9, line 50, after "sequences" please insert --fully--.

In column 36, Claim 10, line 62, after "quences" please insert --fully--.

In column 37, Claim 15, line 40, after "sequences" please insert --fully--.

Signed and Sealed this

Twenty-seventh Day of February, 1996

*Attest:*

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CACATGCAAG TCGAACGGAA AGG                                                      2 3

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GCCCGTATCG CCCGCACGCT CACA                                                2 4

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TCGCGTTGTT CGTGAAATCT CACGGCTTAA                                    3 0

( 2' ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

TCGCGTTGTT CGTGAAAACT CACAGCTTAA                                    3 0

( 2 ) INFORMATION FOR SEQ ID NO:5:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

ACGGGATGCA TGTCTTGTGG TGGAAAGCGC TTTAGC                          3 6

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

ACTTGGCGCA TGCCTTGTGG TGGAAAGCTT         30

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

TTTAGGCGCA TGTCTTTAGG TGGAAAGCTT         30

( 2 ) INFORMATION FOR SEQ ID NO:8:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

TCAAGACGCA TGTCTTCTGG TGGAAAGCTT TTGC         34

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

TCCCGAAGTG CAGGCCAGAT TGCCCACGTG         30

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

GAAGGCTCAC TTTGTGGGTT GACGGTAGGT         30

( 2 ) INFORMATION FOR SEQ ID NO:11:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

GCAATCTGCC TGCACACCGG GATAAGCCTG                                    30

( 2 ) INFORMATION FOR SEQ ID NO:12:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

GGGTCTAATA CCGAATAGGA CCACAGGACA CATG                               34

( 2 ) INFORMATION FOR SEQ ID NO:13:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

TCGCGTTGTT CGTGAAATCT CACAGCTTAA                                    30

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

TCGCGTTGTT CGTGGAATCT CACAGCTTAA                                    30

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

TCGCGTTGTT CGTGGAATGC CACAGCTTAA                                    30

( 2 ) INFORMATION FOR SEQ ID NO:16:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

ATAGGACCAT TCTGCGCATG TGGTGTGGTG                                    30

( 2 ) INFORMATION FOR SEQ ID NO:17:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

ACCTCAAGAC GCATGTCTTC TGGT      24

( 2 ) INFORMATION FOR SEQ ID NO:18:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

CCGAATAGGA CCACAGGACA CATG      24

( 2 ) INFORMATION FOR SEQ ID NO:19:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

ACCTTTAGGC GCATGTCTTT AGGT      24

( 2 ) INFORMATION FOR SEQ ID NO:20:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

AACACTTGGC GCATGCCTTG TGGT      24

( 2 ) INFORMATION FOR SEQ ID NO:21:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

GAAGGCTCAC TTTGTGGGTT GACG      24

( 2 ) INFORMATION FOR SEQ ID NO:22:

( i ) SEQUENCE CHARACTERISTICS:
        ( A ) LENGTH: 24 base pairs
        ( B ) TYPE: nucleic acid
        ( C ) STRANDEDNESS: single (D) TOPOLOGY: linear (ii) MOLECULE TYPE: DNA (genomic)

(xi) SEQUENCE DESCRIPTION: SEQ ID NO:22:

TGTGGTGGAA AGCGCTTTAG CGGT                                                        24

(2) INFORMATION FOR SEQ ID NO:23:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:23:

AGGACCATTC TGCGCATGTG GTGT                                                        24

(2) INFORMATION FOR SEQ ID NO:24:

(i) SEQUENCE CHARACTERISTICS:
      (A) LENGTH: 139 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:24:

CCATCGATAG GACCATTCTG CGCATGTGGT GTGGTGGGTC TAATACCGAA TAGGACCACA              60
GGACACATGA AGGCTCACTT TGTGGGTTGA CGGTAGGTAA CACTTGGCGC ATGCCTTGTG             120
GTGGAAAGCT TCCAAGGCA                                                                139

(2) INFORMATION FOR SEQ ID NO:25:

(i) SEQUENCE CHARACTERISTICS:
      (A) LENGTH: 139 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:25:

TGCCTTGGAA GCTTTCCACC ACAAGGCATG CGCCAAGTGT TACCTACCGT CAACCCACAA              60
AGTGAGCCTT CATGTGTCCT GTGGTCCTAT TCGGTATTAG ACCCACCACA CCACATGCGC             120
AGAATGGTCC TATCGATGG                                                                139

(2) INFORMATION FOR SEQ ID NO:26:

(i) SEQUENCE CHARACTERISTICS:
      (A) LENGTH: 126 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:26:

CCGCTCGAGA CGGGATGCAT GTCTTGTGGT GGAAAGCGCT TAGCGGTAA CTTAGGCGC               60
ATGTCTTTAG GTGGAAAGCT TAACTCAAGA CGCATGTCTT CTGGTGGAAA GCTTTTGCAT            120
CGATGG                                                                              126

(2) INFORMATION FOR SEQ ID NO:27:

( i ) SEQUENCE CHARACTERISTICS:
   ( A ) LENGTH: 126 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:27:

```
CCATCGATGC AAAAGCTTTC CACCAGAAGA CATGCGTCTT GAGTTAAGCT TTCCACCTAA      60
AGACATGCGC CTAAAGTTAC CGCTAAAGCG CTTTCCACCA CAAGACATGC ATCCGTCTC     120
GAGCGG                                                                126
```

( 2 ) INFORMATION FOR SEQ ID NO:28:

( i ) SEQUENCE CHARACTERISTICS:
   ( A ) LENGTH: 29 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:28:

```
GCGGTACCTG CACACAGGCC ACAAGGGAA                                       29
```

( 2 ) INFORMATION FOR SEQ ID NO:29:

( i ) SEQUENCE CHARACTERISTICS:
   ( A ) LENGTH: 31 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO:29:

```
CGCCTGCAGT TAACACATGC AAGTCGAACG G                                    31
```